United States Patent
Lee et al.

(10) Patent No.: US 12,178,833 B2
(45) Date of Patent: Dec. 31, 2024

(54) USE OF MESENCHYMAL STEM CELLS IN TREATING IMMUNE-RELATED DISEASES

(71) Applicant: EMO BIOMEDICINE CORP., New Taipei (TW)

(72) Inventors: Shing-Mou Lee, New Taipei (TW); Hung-Hsuan Chen, New Taipei (TW); Wan-Ling Lai, New Taipei (TW); San-Ni Yu, New Taipei (TW)

(73) Assignee: EMO BIOMEDICINE CORP., New Taipei (TW)

( * ) Notice: Subject to any disclaimer, the term of this patent is extended or adjusted under 35 U.S.C. 154(b) by 474 days.

(21) Appl. No.: 17/434,417

(22) PCT Filed: Sep. 25, 2019

(86) PCT No.: PCT/CN2019/107750
§ 371 (c)(1),
(2) Date: Aug. 27, 2021

(87) PCT Pub. No.: WO2020/232940
PCT Pub. Date: Nov. 26, 2020

(65) Prior Publication Data
US 2022/0133804 A1    May 5, 2022

Related U.S. Application Data

(60) Provisional application No. 62/850,595, filed on May 21, 2019.

(51) Int. Cl.
*A61K 35/12* (2015.01)
*A61K 35/28* (2015.01)
*A61P 19/02* (2006.01)
*A61P 37/06* (2006.01)
*G01N 33/50* (2006.01)

(52) U.S. Cl.
CPC .............. *A61K 35/28* (2013.01); *A61P 19/02* (2018.01); *A61P 37/06* (2018.01); *G01N 33/5073* (2013.01)

(58) Field of Classification Search
CPC ................................................ A61K 2035/122
See application file for complete search history.

(56) References Cited

PUBLICATIONS

Ryan et al., "Interferon-γ does not break but promotes the immunosuppressive capacity of adult human mesenchymal stem cells," Clinical and Experimental Immunology 149:353-363, 2007.*

(Continued)

*Primary Examiner* — Rosanne Kosson
(74) *Attorney, Agent, or Firm* — NZ CARR LAW OFFICE (57) ABSTRACT

Disclosed herein is a method of identifying a plurality of mesenchymal stem cells (MSCs) that are therapeutic to a subject having an immune-related disease, for example, arthritis. According to embodiments of the present disclosure, the MSCs exhibiting to the immune-related disease are characterized in having an immunosuppressive protein binding value (IPBv) greater than 170 toward indoleamine 2,3-dioxygenase (IDO) after being exposed to 50-800 U/ml of IFN-γ. Also disclosed herein are uses of the identified MSCs for the manufacture of a medicament, and methods of treating an immune-related disease by use of the identified MSCs or medicament.

5 Claims, 5 Drawing Sheets

(56) References Cited

PUBLICATIONS

Marufa Rumman, How to calculate IU/ml of IFN-g?, ResearchGate, https://www.researchgate.net/post/How_to_calculate_IU_ml_of_IFN-g, Jan. 20, 2014.*

González et al., Treatment of experimental arthritis by inducing immune tolerance with human adipose-derived mesenchymal stem cells, Arthritis & Rheumatism 60(4):1006-1019, 2009.*

* cited by examiner

USE OF MESENCHYMAL STEM CELLS IN TREATING IMMUNE-RELATED DISEASES

CROSS-REFERENCE TO RELATED APPLICATION

This application is a U.S. National Stage Filing under 35 U.S.C. 371 from International Patent Application Serial No. PCT/CN2019/107750, entitled "USE OF MESENCHYMAL STEM CELLS IN TREATING IMMUNE-RELATED DISEASES," filed on Sep. 25, 2019, and published on Nov. 26, 2020, the disclosure of which are incorporated by reference herein in their entireties."

BACKGROUND OF THE INVENTION

1. Field of the Invention

The present disclosure in general relates to the field of disease treatment. More particularly, the present disclosure relates to methods of identifying a particular population of mesenchymal stem cells (also known as mesenchymal stromal cells; MSCs), and uses of the identified MSCs for the treatment of immune-related diseases, for example, arthritis.

2. Description of Related Art

The immune system is a defense system that protects the subject against various diseases, including pathogen infection (e.g., viral infection, bacterial infection, or fungal infection) and cancers. Depending on the time-course and function of immune response, the immune system may be classified into two immune system, i.e., innate immune system and adaptive immune system (also known as acquired immune system). In general, innate immune system provides a first-line of defense that recruits innate immune cells (including, natural killer cells, eosinophils, basophils, macrophages, neutrophils, and/or dendritic cells) to the target site followed by eliminating the target molecule (e.g., pathogen) via activating a respiratory burst, complement cascade, or adaptive immune system. Compared with the innate immune system, which is non-specific to the target molecule, adaptive immune system is composed of highly specialized immune cells, including T cells and B cells, which specifically target the target molecule. Once activated by innate immune cells, these highly specialized immune cells specifically destroy or inhibit the target molecule by releasing cytotoxin or granzyme to induce cellular necrosis or apoptosis, or by secreting antibodies to promote agglutination, opsonization, neutralization or complement function.

Immune system plays a critical role in maintaining the subject's health. However, it is known that an overactive or uncontrolled immune response may result in excess inflammation thereby causing harmful tissue damage. Nonsteroidal anti-inflammatory drugs (NSAIDs) and immunosuppressants are two mainstreams for treating immune-related diseases. Unfortunately, these treatments do not actually cure the immune-related diseases, but merely provide a temporary relief to the symptoms thereof. Further, the administration of NSAIDs or immunosuppressants may cause undesired side-effect (e.g., gastrointestinal ulcers and bleeds, cardiovascular disease, kidney disease, allergy, and infection), let alone the increased risk of the development of cancers.

In view of the foregoing, there exists in the related art a need for a novel method for treating immune-related diseases in a safer and more accurate manner so as to improve the life quality and life span of the patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of identifying a plurality of mesenchymal stem cells (MSCs) that are therapeutic to a subject having an immune-related disease. The method comprises the steps of, (a) exposing the plurality of MSCs to IFN-γ at the dose of 50-800 U/ml (about 2.5-40 ng/ml);

(b) determining an immunosuppressive protein binding value (IPBv) of the plurality of MSCs toward indoleamine 2,3-dioxygenase (IDO); and (c) identifying the plurality of MSCs that are therapeutic to the subject based on the result determined in the step (b), wherein the MSCs are characterized in having the IPBv greater than 170 toward IDO after being exposed to the IFN-γ at the dose of 50-800 U/ml.

The IPBv of the plurality of MSCs may be determined by any method familiar to one skilled artisan. According to some embodiments, the IPBv of the plurality of MSCs is determined by, (a) adding a first antibody to the plurality of MSCs, wherein the first antibody is specific to the IDO, and has a fluorescent molecule conjugated therewith;

(b) measuring the fluorescence intensity of the product of the step (a); and (c) determining the IPBv of the plurality of MSCs based on the fluorescence intensity measured in the step (b).

In certain embodiments, in the step (c), the IPBv of the plurality of MSCs is determined by the steps of, (c-1) providing a plurality of microbead populations, wherein each microbeads of the plurality of microbead populations has a second antibody coupled thereto, and the number of the second antibody binding to each microbeads in each populations is the same within a population, but is different from population to population among the respective microbead populations, wherein the second antibody is specific to the first antibody;

(c-2) adding the first antibody to the microbead populations of the step (c-1);

(c-3) measuring the fluorescence intensity of the product of the step (c-2);

(c-4) constructing a calibration plot of the number of the second antibody coupled to the microbead populations as a function of the fluorescence intensity determined in the step (c-3); and (c-5) determining the IPBv of the plurality of MSCs from the calibration plot of the step (c-4) based on the fluorescence intensity determined in the step (b).

The MSCs identified by the present method are capable of inhibiting the immune response of the subject thereby alleviating and/or ameliorating the symptoms associated with the immune-related disease. The second aspect of the present disclosure thus is directed to the use of the identified MSCs for the manufacture of a medicament for the treatment of a subject having an immune-related disease.

Also disclosed therein is a method of treating a subject having an immune-related disease. The method comprises administering to the subject an effective amount of the MSCs or medicament of the present disclosure.

According to some embodiments of the present disclosure, the IPBv of the MSCs toward the IDO is greater than 170 after being exposed to the IFN-γ at the dose of 50-800 U/ml.

In general, the immune-related disease treatable by the present MSCs, medicament and/or method is an inflammatory disease (e.g., osteoarthritis (OA) or rheumatoid arthritis (RA)), graft-versus-host disease (GvHD), transplant rejection, or autoimmune disease (e.g., psoriasis). According to some working examples of the present disclosure, the immune-related disease is arthritis.

Depending on intended uses, the MSCs may be autologous, allogeneic or xenogeneic to the subject. Preferably, the MSCs are autologous or allogeneic to the subject.

The subject is a mammal. According to some working examples of the present disclosure, the subject is a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIGS. 3A-3E are results of in vivo analysis according to Example 1.2 of the present disclosure, in which the MSCs having the IPBv higher than 171.6 after the IFN-γ stimulation significantly ameliorated the symptoms of osteoarthritis, and improved the knee function of osteoarthritis patients. FIG. 3A: pain score of arthritis patients assessed by visual analogue scale (VAS) in daily activity. FIG. 3B: pain score of arthritis patients assessed by VAS in sport activity. FIG. 3C: knee function of arthritis patients assessed by international knee documentation committee (IKDC). FIG. 3D: knee function of arthritis patients assessed by knee injury and osteoarthritis outcome score (KOOS). FIG. 3E: magnetic resonance imaging (MRI) score of knees of arthritis patients. Baseline: before the administration of MSCs. **p value<0.01.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "administered," "administering" or "administration" are used interchangeably herein to refer a mode of delivery, including, without limitation, intravenously, intraarticularly, intramuscularly, intraperitoneally, intraarterially, intracranially, or subcutaneously administering an agent (e.g., MSCs) of the present invention.

As used herein, the term "treat," "treating" and "treatment" are interchangeable, and encompasses partially or completely preventing, ameliorating, mitigating and/or managing a symptom, a secondary disorder or a condition associated with immune-related diseases. The term "treating" as used herein refers to the application or administration of MSCs of the present disclosure to a subject, who has a symptom, a secondary disorder or a condition associated with immune-related diseases, with the purpose to partially or completely alleviate, ameliorate, relieve, delay onset of, inhibit progression of, reduce severity of, and/or reduce incidence of one or more symptoms, secondary disorders or features associated with immune-related diseases. Symptoms, secondary disorders, and/or conditions associated with immune-related diseases include, but are not limited to, fatigue, pain, swelling, redness, fever, hair loss, skin rashes, stiffness, tenderness, nausea, cough, shortness of breath, and decreased urine output. Treatment may be administered to a subject who exhibits only early signs of such symptoms, disorder, and/or condition for the purpose of decreasing the risk of developing the symptoms, secondary disorders, and/or conditions associated with immune-related diseases. Treatment is generally "effective" if one or more symptoms or clinical markers are reduced as that term is defined herein. Alternatively, a treatment is "effective" if the progression of a symptom, disorder or condition is reduced or halted.

As used herein, the term "immunosuppressive protein binding value" (IPBv) is used to denote the expression level of an immunosuppressive protein (e.g., IDO molecules) in and/or on a cell (e.g., MSC). According to embodiments of the present disclosure, the IPBv of a cell is determined by the binding capacity of the cell to an antibody, i.e., being determined by the antibody-binding capacity (ABC) of the cell. Specifically, an antibody, which has a reporter molecule (e.g., a fluorescent molecule) conjugated thereto, and exhibits binding affinity and/or specificity to the immunosuppressive molecule (e.g., an anti-IDO antibody), is first added to the cell; after incubating for a period of time and removing unbound antibody, the number of the antibody bound to the cell is quantifying by measuring the level (e.g., the fluorescence intensity) of the reporter molecule via any method familiar to a skilled artisan, for example, flow cytometry, or enzyme-linked immunosorbent assay (ELISA). Based on the binding affinity between the immunosuppressive protein (e.g., the IDO molecule) and the antibody (e.g., the anti-IDO antibody), the cellular expression level of the immunosuppressive protein would be proportional to the measured level of the reporter molecule coupled to the antibody, i.e., the ABC value of the cell, and thus, a skilled artisan may determine the IPBv of the cell in accordance with the thus-determined ABC value. According to some embodiments of the present disclosure, the IPBv is obtained via dividing the ABC value by 1,000.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in cell number, grams, milligrams or micrograms or as milligrams per kilogram of body weight (mg/Kg). Alternatively, the effective amount can be expressed in the concentration of the active component (e.g., MSCs of the present disclosure), such as cell concentration, molar concentration, mass concentration, volume concentration, molality, mole fraction, mass fraction and mixing ratio. Persons having ordinary skills could calculate the human equivalent dose (HED) for the medicament (such as the present MSCs) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

As used therein, the term "autologous" when referring to a biological material (e.g., the MSCs of the present disclosure), indicates that the biological material is derived or isolated from the individual to be treated (e.g., the subject having an immune-related disease). More specifically, the term "autologous" refers to the biological material removed from a donor and administered to a recipient, wherein the donor and recipient are the same individual.

As used herein, the term "allogeneic" when referring to a biological material (e.g., the MSCs of the present disclosure), indicates that the biological material is derived or isolated from a donor who is of the same species as the recipient (e.g., the subject having an immune-related disease), but of different genetic constitution with the recipient. Typically, outbred, non-zygotic twin mammals of the same species are allogeneic with each other. It will be appreciated that an allogeneic donor may be HLA identical or HLA non-identical (i.e., displaying one or more disparate HLA determinants) with respect to the recipient.

The term "xenogeneic" when referring to a biological material (e.g., the MSCs of the present disclosure), indicates that the biological material is derived or isolated from a donor who is of different species as the recipient (e.g., the subject having an immune-related disease). In other words, the term "xenogeneic" refers to transplantation of cells from a donor of one species into a subject of a different species, for example, porcine neural cells can be administered to a subject in an amount suitable to treat chronic pain and/or spasticity.

The term "derived from," when referring to a biological material (e.g., the MSCs of the present disclosure), indicates that the biological material was obtained from the stated source at some point in time. For example, a cell derived from an individual can represent a primary cell obtained directly from the individual (i.e., unmodified).

The term "subject" refers to a mammal including the human species that is treatable with methods of the present invention. The term "subject" is intended to refer to both the male and female gender unless one gender is specifically indicated.

II. Description of The Invention (I) Methods of Identifying MSCs Useful in Treating Immune-Related Diseases The first aspect of the present is directed to a method of identifying a plurality of MSCs that are therapeutic to a subject having an immune-related disease. According to embodiments of the present disclosure, the method comprises, (a) exposing the plurality of MSCs to IFN-γ at the dose of 50-800 U/ml;

(b) determining an IPBv of the plurality of MSCs toward IDO; and (c) identifying the plurality of MSCs that are therapeutic to the subject based on the result determined in the step (b), wherein the MSCs are characterized in having the IPBv greater than 170 toward IDO after being exposed to the IFN-γ at the dose of 50-800 U/ml.

The plurality of MSCs of the present method may be prepared by any method known in the related art, for example, by density gradient separation of adipose tissue (AT), umbilical cord blood (UCB), Wharton's Jelly (WJ) or bone marrow (BM). Depending on intended purposes, the MSCs may be autologous to the subject (i.e., being harvested from the subject having the immune-related disease), allogeneic to the subject (i.e., being harvested from another subject, who is of the same species as the subject having the immune-related disease), or xenogeneic to the subject (i.e., being harvested from a donor that is of a different species relative to the subject having the immune-related disease). Preferably, the MSCs are autologous or allogeneic to the subject. In general, the subject treatable with the MSCs identified by the present method is a mammal, for example, a human, a mouse, a rat, a hamster, a guinea pig, a rabbit, a dog, a cat, a cow, a goat, a sheep, a monkey, and a horse. According to preferred embodiments, the subject is a human.

In the step (a), the MSCs are stimulated by IFN-γ at the dose of 50-800 U/ml (about 2.5-40 ng/ml) so as to produce activated MSCs. According to embodiments of the present disclosure, the administration of a stimulant (i.e., IFN-γ) simulates the microenvironment of the lesion of immune-related diseases thereby providing a potential means to predict the immunosuppressive capacity of MSCs for the treatment of immune-related diseases.

Then, the IPBv of the activated MSCs toward IDO is determined in the step (b). According to certain embodiments of the present disclosure, the IPBv of the activated MSCs is determined by their average antibody binding capacity (ABC). Specifically, an antibody (hereinafter, a first antibody) that exhibits a binding affinity and/or specificity to the IDO molecule (i.e., an anti-IDO antibody, such as a mouse anti-IDO antibody), and has a fluorescent molecule conjugated therewith, is added to the activated MSCs so as to form a MSC immunocomplex. Accordingly, the number of the IDO molecule expressed in and/or on the activated MSCs may be quantified via counting the number of the fluorescent molecules associated with IDO molecule resulted from the binding of the first antibody. Exemplary methods for detecting the fluorescent molecules include, but are not limited to, flow cytometry, fluorescent microscopy, imaging flow cytometry (IFC), fluorometric high-performance liquid chromatography (HPLC), magnetic modulation biosensing, and fluorescence resonance energy transfer (FRET). According to some preferred examples of the present disclosure, the fluorescent molecules are detected by flow cytometry.

As would be appreciated, the fluorescent molecule may be any molecule that may re-emit light upon light excitation, for example, green fluorescent protein (GFP), enhanced green fluorescent protein (eGFP), red fluorescent protein (RFP), yellow fluorescent protein (YFP), fluorescein isothiocyanate (FITC), phycoerythrin (PE), and allophycocyanin (APC). In one working example of the present disclosure, the fluorescent molecule is PE.

It would be appreciated that instead of the fluorescent molecule, the first antibody may alternatively conjugated with other reporter molecules, e.g., a quantum dot, as long as such reporter molecules are countable by suitable assays.

According to certain embodiments of the present disclosure, the average ABC of the activated MSCs (i.e., the binding capacity of the activated MSCs to the first antibody) is determined by a plurality of microbead populations, wherein each microbead of the plurality of microbead populations has a diameter substantially equivalent to the average diameter of the MSCs, and has a second antibody specific to the first antibody (such as an anti-mouse antibody) coupled thereto. In these embodiments, a total of four microbead populations are prepared, in which each microbead in the first microbead population has a first ABC number (such as 12,257) of the second antibody coupled thereto, i.e., each microbead has 12,257 of the second antibody coupled thereto and thus is capable of binding to 12,257 of the first antibody; each microbead in the second microbead population has a second ABC number (such as 72,745) of the second antibody coupled thereto, i.e., each microbead has 72,745 of the second antibody coupled thereto, and thus is capable of binding to 72,745 of the first antibody; each microbead in the third microbead population has a third ABC number (such as 283,360) of the second antibody coupled thereto, i.e., each microbead has 283,360 of the second antibody coupled thereto, and thus is capable of binding to 283,360 of the first antibody; and each microbead in the fourth microbead population has a fourth ABC number (such as 886,417) of the second antibody coupled thereto, i.e., each microbead has 886,417 of the second antibody coupled thereto, and thus is capable of binding to 886,417 of the first antibody.

The fluorescent molecule-conjugated first antibody (e.g., the PE-conjugated mouse anti-IDO antibody) is added to the first to the fourth microbead populations thereby forming a first, second, third, and fourth control immunocomplexes. The average fluorescent intensities of the first to the fourth control immunocomplexes may be determined by any method discussed above, for example, flow cytometry. Based on the binding affinity between the first antibody (e.g., the mouse anti-IDO antibody) and the second antibody (e.g., the anti-mouse antibody), the number of the second antibody coupled to the microbead populations would be proportional to the average fluorescence intensity of the control immunocomplexes. A calibration plot may thus be constructed, in which the x-coordinate corresponds to the average fluorescence intensity of the control immunocomplexes, and the y-coordinate corresponds to the number of the second antibody coupled to the microbead populations. The average ABC of the activated MSCs to the first antibody are accordingly determined from the calibration plot based on the fluorescence intensity thereof. Then, the IPBv of the activated MSCs is obtained via dividing the average ABC by 1,000 (i.e., IPBv=the average value of ABC/1,000).

Next, in the step (c), the MSCs suitable for treating the immune-related disease are identified based on the IPBv of the activated MSCs determined in the step (b). According to some embodiments of the present disclosure, after being stimulated with 50-800 U/ml of IFN-γ in the step (a), the MSCs having an IPBv greater than 170 (e.g., 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or more) are identified as being useful in treating the immune-related disease.

According to some embodiments, the MSCs are stimulated with 50 U/ml (2.5 ng/ml) of IFN-γ; in these embodiments, the MSCs having an IPBv greater than 170 are identified as being therapeutic to the immune-related disease. According to certain examples, after being stimulating with 50 U/ml of IFN-γ, the MSCs having an IPBv greater than 171.6 are identified as being therapeutic to the immune-related disease In some specific examples, MSCs having an IPBv ranging between 171.6 to 378.5 under the stimulation of 50 U/ml of IFN-γ are identified as useful MSCs for the treatment of the immune-related disease.

According to alternative embodiments, the MSCs are stimulated with 800 U/ml (40 ng/ml) of IFN-γ; in these embodiments, the MSCs having an IPBv greater than 400 are identified as being therapeutic to the immune-related disease. According to certain examples, after being stimulating with 800 U/ml of IFN-γ, the MSCs having an IPBv greater than 423.4 are identified as being therapeutic to the immune-related disease. In some specific examples, the MSCs having an IPBv ranging between 423.4 to 648.5 under the stimulation of 800 U/ml of IFN-γ are identified as useful MSCs for the treatment of the immune-related disease.

Based on the correlation of the IPBv and therapeutic effect of MSCs, also disclosed herein is the use of IPBv serving as a biomarker for the manufacture of a kit. The use of the present disclosure is characterized in that,

- the biomarker is an IPBv of a plurality of MSCs toward IDO; and
- the kit is useful in making a prognosis of whether the plurality of MSCs are therapeutic to a subject having an immune-related disease, wherein when the plurality of MSCs are exposed to IFN-γ at the dose of 50-800 U/ml, the IPBv greater than 170 indicates that the plurality of MSCs are therapeutic to the subject.

The method for determining the IPBv of MSCs are similar to the above-mentioned method, and hence, detailed description thereof is omitted herein for the sake of brevity.

The immune-related disease treatable by the identified MSCs may be any disease, disorder, or condition, which is caused by and/or associated with immune response, especially the disease, disorder, or condition caused by and/or associated with overactive immune response, for example, an inflammatory disease, GvHD, transplant rejection, or autoimmune disease. Examples of inflammatory disease treatable with the present MSCs include, but are not limited to, arthritis, asthma, inflammatory bowel disease (IBD), ulcerative colitis, atherosclerosis, multiple sclerosis, chronic obstructive pulmonary disease (COPD), atopic dermatitis (AD), infection, and sepsis. Exemplary autoimmune diseases treatable with the present MSCs include, but are not limited to, systemic lupus erythematosus (SLE), psoriasis, scleroderma, uveitis, insulin dependent diabetes mellitus, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, and autoimmune uveitis. According to certain embodiments of the present disclosure, the immune-related disease is arthritis, for example, osteoarthritis (OA), rheumatoid arthritis (RA), psoriatic arthritis, traumatic arthritis, septic arthritis, ankylosing spondylitis, and juvenile idiopathic arthritis. In one working example, the immune-related disease is osteoarthritis.

(II) Methods of Treating Immune-Related Diseases

The second aspect of the present disclosure is directed to the use of the MSCs as identified in Part (I) of the present disclosure for the manufacture of a medicament for the treatment of a subject having an immune-related disease.

The present disclosure also provides a method of treating an immune-related disease in a subject by use of the present MSCs or medicament. Specifically, the method comprises administering to the subject an effective amount of the MSCs or the medicament of the present disclosure.

As mentioned in Part (I) of the present disclosure, said MSCs are characterized in having an IPBv greater than 170 toward IDO after being exposed to 50-800 U/ml of IFN-γ;

According to some embodiments of the present disclosure, the naïve MSCs (i.e., the MSCs not treated with IFN-γ or any stimulus), which have an IPBv greater than 170 toward IDO after being exposed to 50-800 U/ml of IFN-γ, are administered to the subject so as to ameliorate and/or alleviate the symptoms associated with the immune-related disease. Preferably, the IPBv of the administered MSCs toward the IDO is greater than 170 after being exposed to 50 U/ml of IFN-γ, or is greater than 400 after being exposed to 800 U/ml of IFN-γ. More preferably, the IPBv of the administered MSCs toward the IDO is greater than 171.6 after being exposed to 50 U/ml of IFN-γ, or is greater than 423.4 after being exposed to 800 U/ml of IFN-γ. In certain working examples, the IPBv of the administered MSCs toward the IDO is ranged from 171.6 to 378.5 after being exposed to 50 U/ml of IFN-γ. In alternative examples, the IPBv of the administered MSCs toward the IDO is ranged from 423.4 to 648.5 after being exposed to 800 U/ml of IFN-γ.

According to some embodiments of the present disclosure, the subject is a human, and about $1\times10^5$ to $1\times10^9$ of the MSCs are administered to the subject. Preferably, the effective amount is about $1\times10^6$ to $1\times10^8$ of the MSCs. According to some working examples, $5\times10^7$ of the MSCs are sufficient to produce a therapeutic effect on the subject.

For the purpose of efficiently ameliorating and/or alleviating the symptoms associated with the immune-related disease, the MSCs or medicament of the present disclosure may be administered to the subject one or more times. For example, the MSCs or medicament of the present disclosure may be administered once for a full course of treatment. Alternatively, the MSCs or medicament of the present disclosure may be administered to the subject once every day, every two days, every three days, every four days, every five days, every six days, every week, every two weeks, every three weeks, every month, every two months, every three months, every fourth months, every five months, or longer period of time (e.g., once per year).

Depending on intended uses, the administered MSCs may be autologous, allogeneic or xenogeneic to the subject.

The MSCs and/or medicament may be administered to the subject via any suitable route, for example, intraarticular, subcutaneous, intravenous, bolus injection, intramuscular, or intra-arterial injection. According to some working examples, the MSCs are administered to the subject have arthritis via intraarticular injection thereby ameliorating and/or alleviating the symptoms associated with the arthritis.

As could be appreciated, the amount, route of administration, and dosing schedule of the present MSCs or medicament may vary with factors such as the disease or specific symptoms to be treated, prevented, or managed, and the age, sex and condition of the patient. The roles played by such factors are well known in the art, and may be accommodated by routine experimentation.

As would be appreciated, the present method can be applied to the subject, alone or in combination with additional therapies that have some beneficial effects on the treatment of immune-related diseases, for example, NSAIDs or immunosuppressants. Depending on the intended purpose, the present method can be applied to the subject before, during, or after the administration of the additional therapies.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Cultivation of MSCs

Human fat tissue was washed with Dulbecco's phosphate-buffered saline (DPBS) for several times to remove contaminating red blood cells (RBCs), and then digested with 0.1% type I collagenase in a water bath at 37° C. After complete digestion, pelleted stromal vascular fraction (SVF) was collected by centrifugation and seeded in culture flasks. The cells were maintained in a humidified tissue culture incubator at 37° C. with 5% $CO_2$. After overnight incubation, the cells were washed with DPBS to remove floating cells and cell debris, and then the fresh medium was added to the culture flasks. The culture medium was replaced by fresh medium every 2-3 days until the cells reach 80-90% confluence. MSCs were harvested by trypsinized and reseeded to the new culture flasks. At the end of cultivation, MSCs were suspended in a cryopreservation medium including 10% DMSO and stored frozen in liquid nitrogen.
IDO Quantification Assay
1. Priming Cells Cells were seeded into the flask at 50,000 cells/$cm^2$ and primed with IFN-γ at 50, 200 or 800 U/ml for 24 hours. Then, cells were harvested for cell membrane or intracellular protein staining and quantified IDO by comparing the fluorescent intensity of bound anti-IDO antibody on cells to the fluorescent intensity of the Quantum Simply Cellular (QSC) beads stained with the same fluorescent conjugated anti-IDO antibody.
2. Intracellular Protein Staining Primed cells were fixed by fixation buffer at 4° C. for 20 minutes and then washed by staining buffer (DPBS with 1% FBS) two times. Fixed cells were centrifuged and removed the supernatant, then suspended in a permeabilization buffer at 4° C. for 15 minutes. The fixed/permeabilized cells were thoroughly resuspended in 50 μL of the permeabilization buffer containing anti-IDO antibody, and incubated at 4° C. for 30 minutes in the dark. The cells were washed for two times with the permeabilization buffer followed by resuspending in staining buffer for flow cytometry analysis.
3. Quantification by QSC Beads The QSC beads consisted of four beads populations, wherein each bead of the first bead population had 12,257 goat anti-mouse antibody covalently bound onto the surface, each bead of the second bead population had 72,745 goat anti-mouse antibody covalently bound onto the surface, each bead of the third bead population had 283,360 goat anti-mouse antibody covalently bound onto the surface, and each bead of the fourth bead population had 886,417 goat anti-mouse antibody covalently bound onto the surface. The beads of the four beads populations mixture were capable of capturing fluorescent-labeled mouse anti-human IDO antibody. The QSC beads were stained with anti-human IDO antibody for 30 minutes and then washed with 1 ml staining buffer for two times. The beads were then resuspended in the staining buffer for flow cytometry analysis.

Geometric mean fluorescence intensity (Geo MFI) of the MSCs and QSC beads were acquired by flow cytometry. A linear regression curve was constructed by plotting the Geo MFI of the QSC beads against the manufacture-assigned ABC values of the QSC beads. The ABC value of MSC was determined by comparing its Geo MFI against the standard curve, and the IPBv was then obtained via dividing the ABC value by 1,000 (i.e., IPBv=average ABC/1,000).

Treatment of Knee Osteoarthritis with Autologous MSC

Twelve subjects with moderate to severe knee osteoarthritis were recruited by informed consent. The adipose tissues taken from subjects were transported to a collaborated manufacturer for MSC preparation. $5 \times 10^7$ of the isolated and expanded MSCs were prepared for one dose injection. The prepared MSCs were cryopreserved in a liquid nitrogen tank until use. Only MSCs that complied with all releasing tests (including seven items of releasing tests) were intraarticularly administrated to the knee of a recruited subject. All subjects were observed for primary and secondary endpoints after one, four, twelve, twenty-four and forty-eight weeks after the MSCs injection. Primary and secondary endpoints respectively represented checks of safety and efficacy. Safety endpoint includes physical examination, check of vital signs, routine laboratory tests, and record of adverse events by common terminology criteria for adverse events version 4.0 made by National Cancer Institute (NCI-CTCAE v4.0). Efficacy endpoint includes the following examinations:

(A) Classification of knee osteoarthritis, which was measured with Kellgren Lawrence grading system by X-ray, and assigned a grade from 0 to 4.

(B) Articular cartilage quality, which was evaluated by MRI, and graded by two doctors via evaluating the MOAKS (MRI Osteoarthritis Knee Score).

(C) Pain, which was assessed by VAS (Visual Analogue Scale) in daily and sports activities, and scored on a scale from 0 to 100.

(D) Knee function, which was assessed by IKDC and KOOS questionnaires, and scored on a scale from 0 to 100.

Example 1 Characterization of MSCs 1.1 Determining Average ABC of MSCs

Figure 1A:
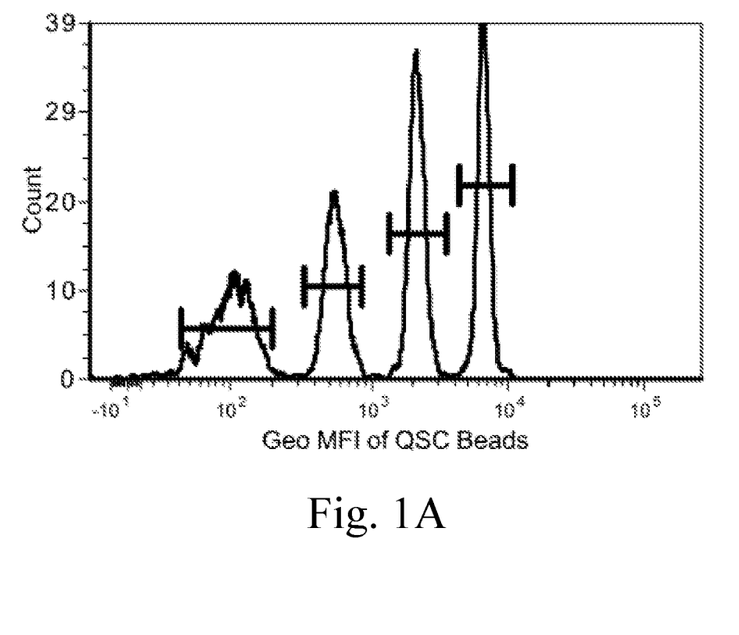
FIG. 1A is the result of flow cytometry according to Example 1.1 of the present disclosure.
Figure 1B:
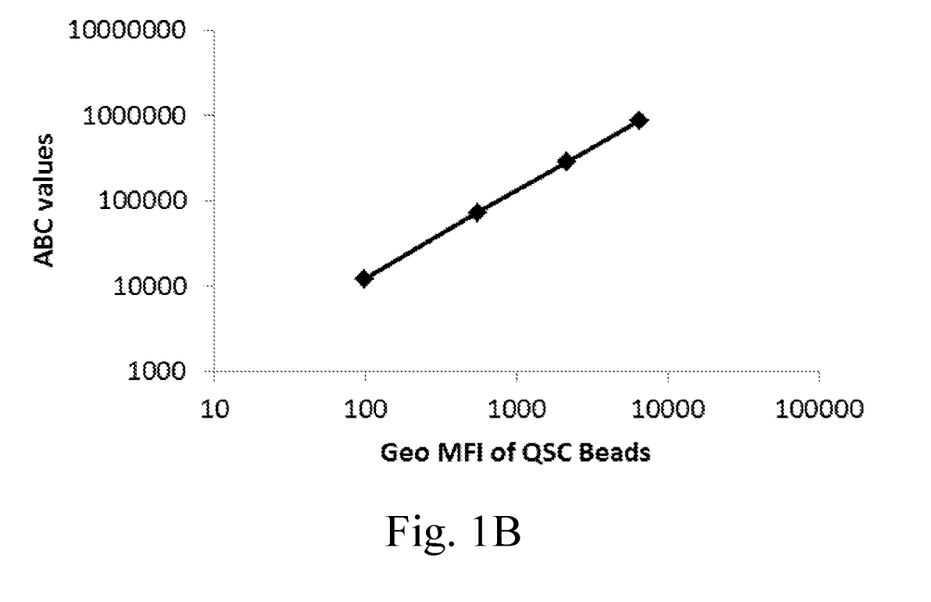
FIG. 1B is a calibration plot depicting the correlation between the fluorescence intensity and the number of quantum simply cellular (QSC) beads according to Example 1.1 of the present disclosure.

For the purpose of evaluating the effect of MSC on immune-related diseases, the IPBv of MSCs were first determined by QSC beads. As described in Materials and Methods, the QSC beads consisted of four bead populations, each of which had specified number of the goat anti-mouse antibody bound therewith. After mixing the fluorescent-labeled mouse anti-human IDO antibody, four populations with different fluorescence intensities were detected (FIG. 1A). Then, a calibration plot was constructed based on the fluorescence intensities of the QSC beads and the number of the goat anti-mouse antibody bound with the QSC beads (FIG. 1B).

Figure 2A:
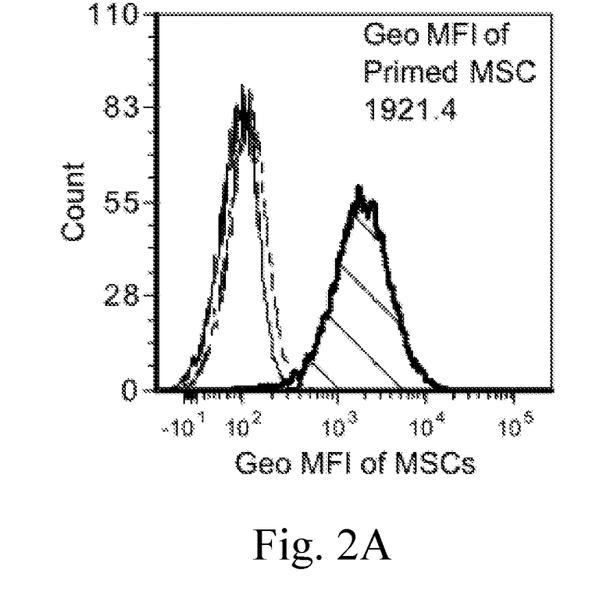
FIGS. 2A-2C are results of flow cytometry according to Example 1.1 of the present disclosure that respectively depict the fluorescence intensities of MSCs stimulated with IFN-γ at the dose of 50 U/ml (FIG. 2A), 200 U/ml (FIG. 2B), and 800 U/ml (FIG. 2C).
Figure 2B:
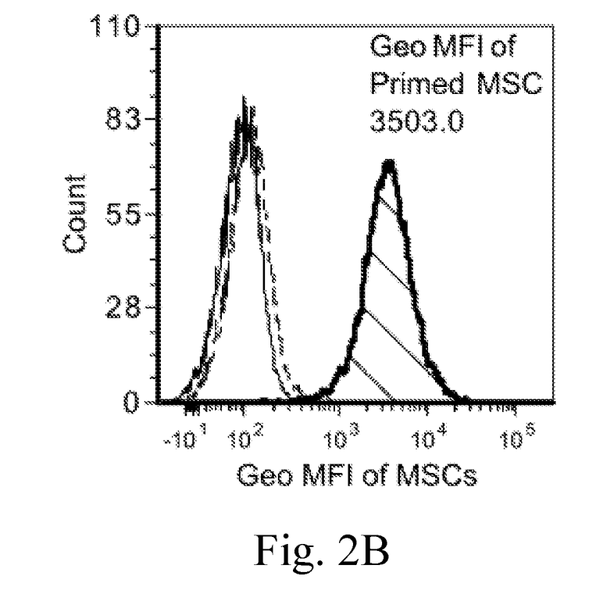
Figure 2C:
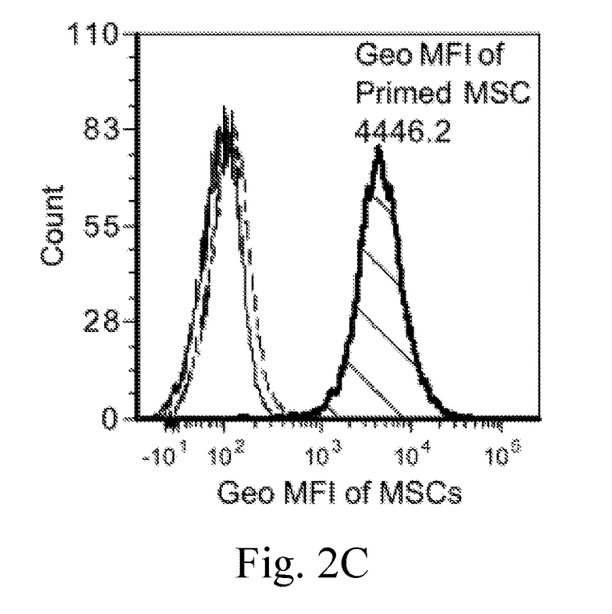
Figure 3A:
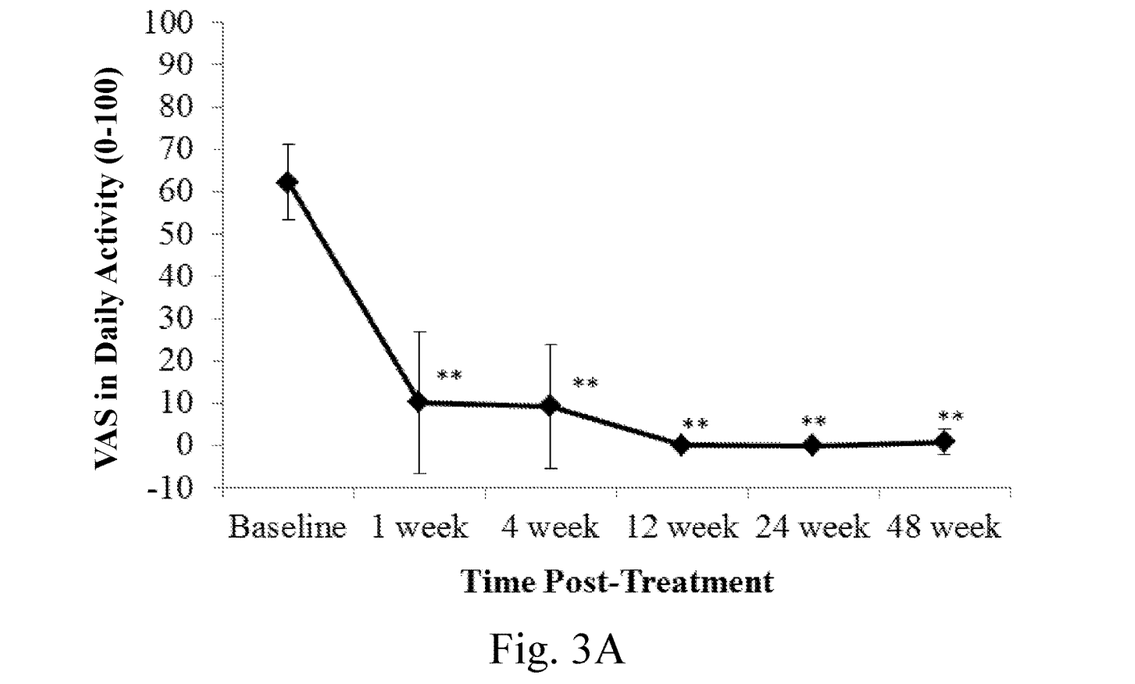
Figure 3B:
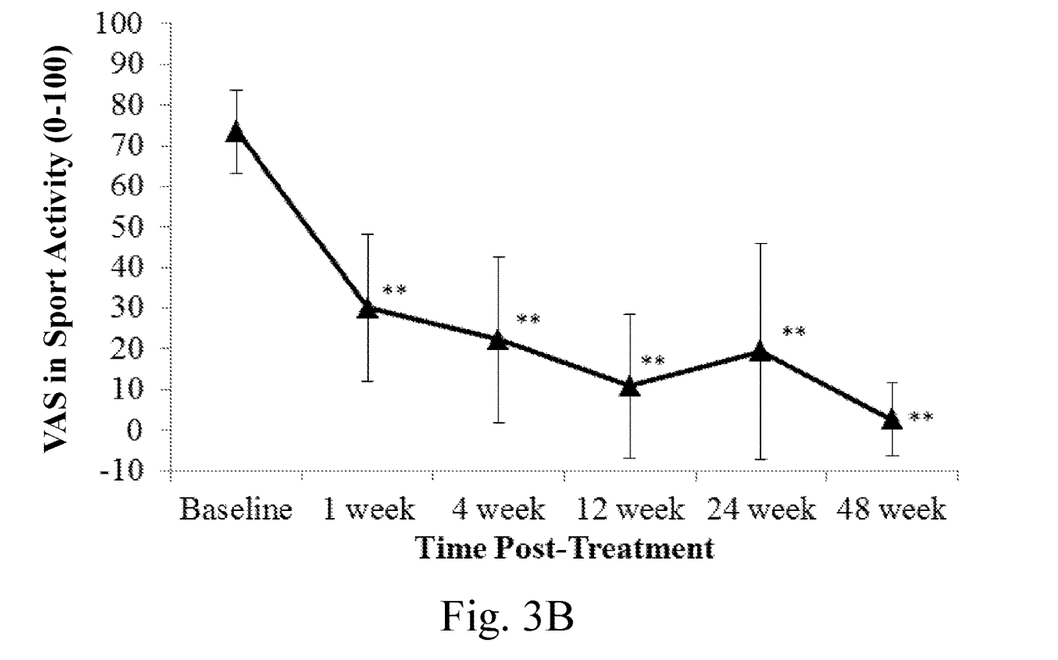
Figure 3C:
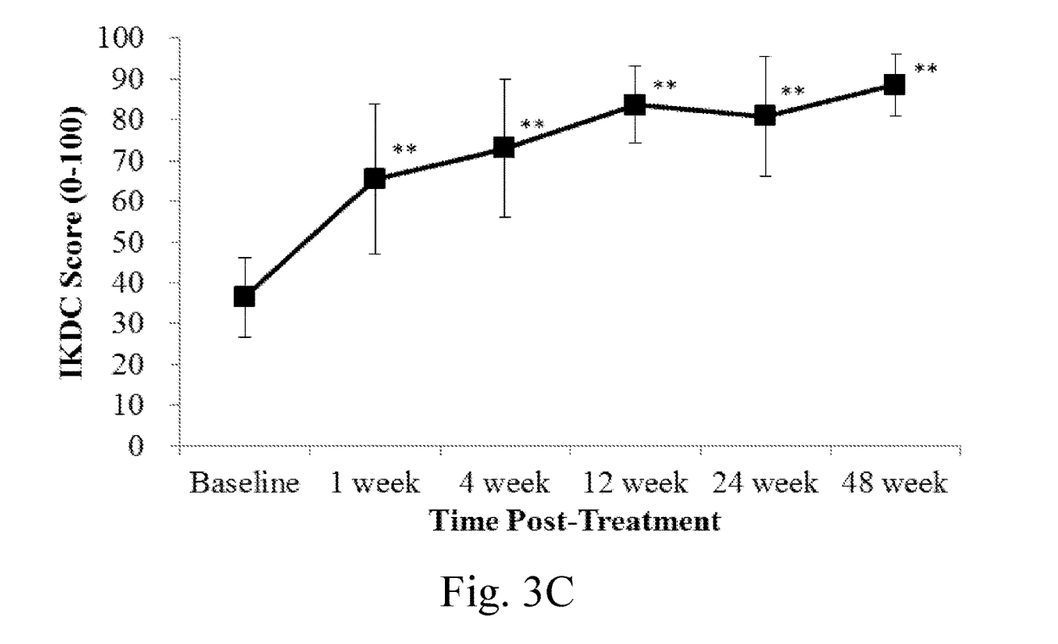
Figure 3D:
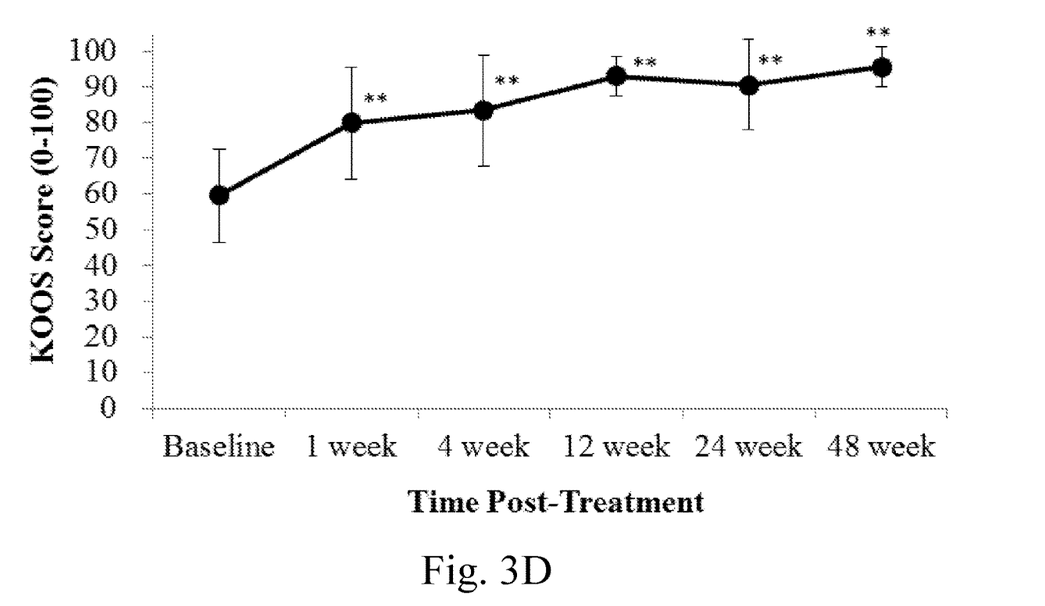
Figure 3E:
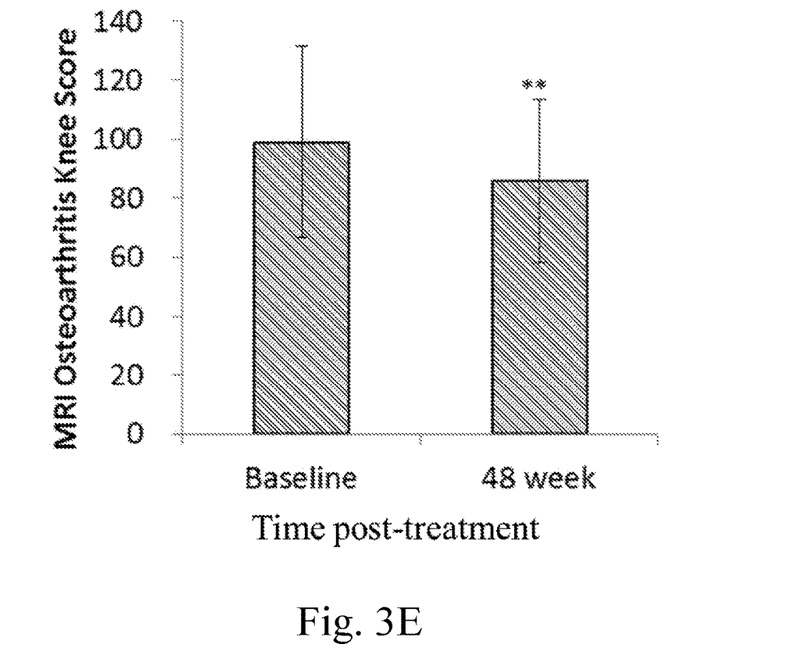

On the other hand, the fluorescence intensities of MSCs stimulated by various concentration of IFN-γ (i.e., 50, 200, or 800 U/ml) were determined by flow cytometry, and the results are illustrated in FIGS. 2A-2C. The average ABCs and IPBv of the IFN-γ-primed MSCs were then determined by the calibration plot based on the fluorescence intensities thereof. The data is summarized in Table 1.

TABLE 1

Average ABC and IPBv of MSCs stimulated by specified concentration of IFN-γ

| IFN-γ concentration (U/ml) | Fluorescence Intensity | Average ABC | IPBv |
|---|---|---|---|
| 50 | 1921.4 | 254,466 | 254.5 |
| 200 | 3503.0 | 469,222 | 469.2 |
| 800 | 4446.2 | 598,250 | 598.3 |

1.2 In Vivo Analysis

Whether the IPBv of MSCs is correlated to their therapeutic effect was evaluated in this example. As mentioned in Materials and Methods, the MSCs were respectively prepared from twelve subjects having moderate to severe knee osteoarthritis. After being activated by 50, 200 or 800 U/ml of IFN-γ for 24 hours, the activated MSCs were subjected to flow cytometry thereby determining the IPBv thereof. The data of Table 2 indicated that the therapeutic effect of MSCs on arthritis was positively correlated with the IPBv of the activated MSCs, in which compared with other concentrations, the highest correlation coefficient between the IDO expression and the VAS-sport (week 12) was observed in the MSCs stimulated with 50 U/ml IFN-γ, while the highest correlation coefficient between the IDO expression and the improvement of knee function (including IKDC and KOOS assessments, week 12) was observed in the MSCs stimulated with 800 U/ml IFN-γ.

Based on the results of Table 2, two linear regression formulas were established. The correlation between the IDO expression and the VAS-sport was represented in formula (I):

$$y = 37.1 + \frac{61.4}{1 + \left(\frac{x}{171.6}\right)^{-91.8}}, \tag{I}$$

wherein the x-value represented the IPBv of the MSCs after being stimulated with 50 U/ml of IFN-γ, and the y-value represented the score of the subject in the VAS-sport assessment (from 0 to 100) twelve weeks after the MSC administration. According to formula (I), when the score of the VAS-sport assessment was set to 50, then an x-value of 171.6 was obtained. Compared with the MSCs having an IPBv less than 171.6, the MSCs having an IPBv higher than 171.6 after the IFN-γ treatment obviously relieved the pain of arthritis patients (Table 2).

The correlation between the IDO expression and the improvement of knee function was represented in formula (II):

$$y = 36.6 + \frac{43.6}{1 + \left(\frac{x}{423.4}\right)^{-20.1}}, \tag{II}$$

wherein the x-value represented the IPBv of the MSCs after being stimulated with 800 U/ml of IFN-γ, and the y-value represented the score of the subject in the IKDC assessment (from 0 to 100) twelve weeks after the MSC administration. According to formula (II), when the score of the IKDC assessment was set to 50, then an x-value of 423.4 was obtained. Compared with the MSCs having IPBv less than 423.4, the MSC having an IPBv higher than 423.4 after IFN-γ treatment obviously improved the knee function of arthritis patients (Table 2).

TABLE 2

Correlation of IDO expression and therapeutic effect of MSCs on arthritis

| | IDO Quantification | | | Clinical Outcome at Week 12 | | |
|---|---|---|---|---|---|---|
| | IPBv | | | VAS-Sport | IKDC | KOOS |
| | | | | | Knee Function | |
| Subject No. | 50 U/ml IFN-γ | 200 U/ml IFN-γ | 800 U/ml IFN-γ | Pain Relief % | Improvement % | |
| 02 | 254.5 | 469.2 | 598.3 | 100.0 | 100.0 | 100.0 |
| 04 | 169.2 | 389.6 | 479.5 | 50.0 | 52.7 | 75.9 |
| 05 | 301.3 | 485.3 | 558.7 | 97.5 | 65.6 | 81.8 |
| 06 | 323.5 | 583.5 | 648.5 | 100.0 | 83.3 | 83.5 |
| 07 | 378.5 | 556.1 | 608.2 | 100.0 | 74.6 | 82.8 |
| 08 | 377.7 | 598.9 | 645.9 | 88.2 | 81.3 | 87.4 |
| 09 | 130.7 | 270.3 | 338.0 | 43.3 | 37.5 | 43.1 |
| 10 | 235.3 | 444.3 | 517.5 | 100.0 | 91.9 | 98.5 |
| 11 | 209.7 | 388.6 | 458.5 | 100.0 | 82.4 | 95.1 |
| 12 | 121.1 | 301.5 | 419.5 | 30.8 | 54.1 | 60.3 |
| 13 | 243.5 | 391.7 | 463.2 | 100.0 | 80.4 | 96.2 |
| 16 | 305.2 | 562.2 | 632.8 | 100.0 | 74.2 | 80.8 |
| Correlation coefficient between IDO and Clinical Outcome (p value) | | | 50 U/ml IFN-γ | 0.750 (0.005) | 0.554 (0.062) | 0.502 (0.096) |
| | | | 200 U/ml IFN-γ | 0.706 (0.010) | 0.584 (0.046) | 0.510 (0.090) |
| | | | 800 U/ml IFN-γ | 0.679 (0.015) | 0.639 (0.025) | 0.548 (0.065) |

The MSCs, which had an IPBv higher than 171.6 after 50 U/ml IFN-γ treatment or had an IPBv higher than 423.4 after 800 U/ml IFN-γ treatment, were intraarticularly administered to the subject's knee. The data of FIGS. 3A-3E demonstrated that such the MSCs effectively ameliorated the symptoms (i.e., pain) of osteoarthritis, and improved the knee function of the subject.

In conclusion, the present disclosure provides a method for identifying a plurality of MSCs for the treatment of immune-related diseases, for example, arthritis. The thus-identified MSCs had an IPBv higher than 171.6 after being activated by 50 U/ml of IFN-γ, or had an IPBv higher than 423.4 after being activated by 800 U/ml of IFN-γ. Compared to the MSCs not fulfilling the criteria set out above, the MSCs identified by the present method obviously ameliorated the symptoms of the immune-related disease, and accordingly, are useful for the development of medicaments for the treatment or prophylaxis of immune-related diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject having an immune-related disease, comprising administering to the subject a therapeutically effective amount of a composition comprising activated mesenchymal stem cells (MSCs), wherein the activated MSCs are made by incubating them with IFN-γ at a dose of 50-800 U/ml, wherein the activated MSCs have having an immunosuppressive protein binding value (IPBv) greater than 170 toward indoleamine 2,3-dioxygenase (IDO), and wherein the IPBv of the activated MSCs is determined by:
   (a) adding a first antibody to the MSCs, wherein the first antibody is specific to the IDO, and has a fluorescent molecule conjugated therewith;
   (b) providing a plurality of microbead populations, wherein each microbead in each population of the plurality of microbead populations has a second antibody coupled thereto, wherein the number of second antibodies coupled to each microbead in each population is the same within one population but is different from the number of coupled second antibodies in each different population in the plurality of populations, and wherein the second antibody is specific to the first antibody;
   (c) adding the MSC-first antibody composition made in step (a) to the mixture of microbead populations of step (b);
   (d) measuring the fluorescence intensity of each microbead population made in step (c);
   (e) constructing a calibration plot of the number of the second antibody coupled to the microbead populations as a function of the fluorescence intensity determined in step (d); and
   (f) determining the IPBv of the activated MSCs from the calibration plot of step (e) based on the fluorescence intensity determined in step (d).

2. The method of claim 1, wherein the immune-related disease is arthritis.

3. The method of claim 1, wherein the MSCs are autologous to the subject.

4. The method of claim 1, wherein the MSCs are allogeneic to the subject.

5. The method of claim 1, wherein the subject is a human.

\* \* \* \* \*